(12) United States Patent
Burbank et al.

(10) Patent No.: US 6,258,079 B1
(45) Date of Patent: Jul. 10, 2001

(54) METHOD AND SYSTEMS FOR ESTABLISHING VASCULAR ACCESS

(75) Inventors: Jeffrey H. Burbank, Boxford; James M. Brugger, Newburyport; Charles D. Finch, Clinton, all of MA (US); Gerald Beathard, Austin, TX (US); George W. Buffaloe, Arvada, CO (US)

(73) Assignee: Vasca, Inc., Tewksbury, MA (US)

( * ) Notice: Subject to any disclaimer, the term of this patent is extended or adjusted under 35 U.S.C. 154(b) by 0 days.

(21) Appl. No.: 09/333,828

(22) Filed: Jun. 15, 1999

Related U.S. Application Data

(63) Continuation-in-part of application No. 08/856,641, filed on May 15, 1997, now Pat. No. 5,931,829.
(60) Provisional application No. 60/036,124, filed on Jan. 21, 1997.

(51) Int. Cl.[7] ................................................. A61M 31/00
(52) U.S. Cl. .............................. 604/502; 604/4; 604/93
(58) Field of Search ............................... 604/4, 93, 5–7, 604/500, 502, 506–509, 264, 523, 533, 534, 513, 247, 539

(56) References Cited

U.S. PATENT DOCUMENTS

| | | |
|---|---|---|
| 4,181,132 | 1/1980 | Parks . |
| 4,892,518 | 1/1990 | Cupp et al. . |
| 5,041,098 | 8/1991 | Loiterman et al. . |
| 5,152,747 | 10/1992 | Oliver . |
| 5,203,771 | 4/1993 | Melker et al. . |
| 5,215,530 | 6/1993 | Hogan . |
| 5,234,406 | 8/1993 | Drasner et al. . |
| 5,281,199 | 1/1994 | Ensminger et al. . |
| 5,417,656 | 5/1995 | Ensminger et al. . |
| 5,562,617 | 10/1996 | Finch, Jr. et al. . |

FOREIGN PATENT DOCUMENTS

| | | |
|---|---|---|
| 0564321 | 10/1993 | (EP) . |
| WO 93/00129 | 1/1993 | (WO) . |

*Primary Examiner*—Wynn Wood Coggins
*Assistant Examiner*—Deborah Blyveis
(74) *Attorney, Agent, or Firm*—Townsend and Townsend and Crew LLP

(57) ABSTRACT

A body lumen access system comprises a distal access cannula and a proximal access cannula. The distal access cannula is attached to or within the body lumen and the proximal access cannula is attached to an implantable port or is transcutaneously positioned and attached to a luer or other external connector. The distal and proximal access cannulas are usually implanted separately, cut to length, and attached at a subcutaneous junction location. Preferably, the proximal access cannula has a larger lumen diameter than that of the distal access cannula in order to reduce flow resistance within the cannula system. In some cases the distal and proximal access cannulas may be formed integrally. Replacement of a proximal portion or distal end may be performed by accessing the cannula, removing either the proximal portion or distal end, and reattaching a replacement portion of the cannula.

10 Claims, 20 Drawing Sheets

METHOD AND SYSTEMS FOR ESTABLISHING VASCULAR ACCESS

CROSS-REFERENCES TO RELATED APPLICATIONS

The present application is a continuation-in-part of application Ser. No. 08/856,641, filed on May 15, 1997, now U.S. Pat. No. 5,931,829 the full disclosure of which is incorporated herein by reference. This application claims benefit of provisional application 60/036,124, filed Jan. 21, 1997.

BACKGROUND OF THE INVENTION

1. Field of the Invention

The present invention relates generally to the design and use of medical devices, and more particularly to a method and system for establishing temporary access to a patient's vascular system for hemodialysis and other extracorporeal blood treatments.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications which are limited in time, such as intravenous feeding, intravenous drug delivery, and the like, they are not suitable for hemodialysis and other extracorporeal procedures that must be repeated periodically, often for the lifetime of the patient.

For hemodialysis and other extracorporeal treatment regimens, a variety of transcutaneous catheters and implantable ports have been proposed over the years. Transcutaneous catheters, such as the Tesio catheter available from Med Comp and the Perm-Cath™ available from Quinton, comprise a single catheter tube having a distal end placed in a vein in an in-dwelling manner and a proximal end which extends through the skin and is which available for connection to a hemodialysis or other blood treatment system. Such catheter includes a DACRON® cuff disposed just beneath the skin in order to reduce the risk of infection.

Implantable ports, in contrast, are entirely subcutaneous and connected to a vein or an artery by a subcutaneous cannula. Access to the port is achieved by percutaneous placement of a needle or other connecting tube. Such ports typically comprise a needle-penetrable septum to permit percutaneous penetration of the needle. Recently, several valved-port designs have been proposed, where introduction of a needle or other access tube opens the valve to provide flow to the cannula which connects to the blood vessel.

Both the transcutaneous and implanted port vascular access systems suffer from certain disadvantages and limitations. A particular problem with prior transcutaneous and implanted port vascular access systems has been replacement. It is often necessary to replace a transcutaneous catheter when its distal end becomes dysfunctional due to plugging or other causes. Heretofore, it has usually been necessary to remove the entire catheter, including the subcutaneous cuff which has become ingrown in the tissue. In the case of implanted port systems, either the port or the cannula attached to the blood vessel could become dysfunctional. Heretofore, it has generally been necessary to remove both the port and the implanted cannula when either needs to be replaced.

It would therefore be desirable to provide improved methods, systems, and kits which permit only a portion of an implanted system to be replaced when other portions of the system remain functional. Such improved methods, systems, and kits should both simplify such replacement procedures and reduce trauma to patient's undergoing such procedures. In addition, it would be desirable if the improved methods, systems, and kits were useful with a wide variety of implantable catheters (including at least subcutaneous catheters and transcutaneous catheters used for vascular access), were easy to use, and could reduce costs associated with long term maintenance of such implantable access devices. At least some of these objectives will be met by the different aspects of the present invention described below.

2. Description of the Background Art

U.S. Pat. Nos. 5,562,617 and 5,041,098 are exemplary of implantable systems employing cannulas extending between a port and a blood vessel for providing extracorporeal circulation. U.S. Pat. Nos. 5,417,656 and 5,281,199 show implantable ports which are connected to vascular cannulas via a transition region (FIG. 1A) and to a multiple branch cannula (FIG. 21). U.S. Pat. No. 4,892,518 shows an implanted port with a transition region extending to a cannula. U.S. Pat. Nos. 5,234,406 and 5,215,530 show two-piece catheters having a distal portion which can be placed percutaneously. The '406 patent discloses a large diameter proximal portion to enhance the flow rate of anesthetics to the subarachnoid region of the spine. U.S. Pat. Nos. 5,203,771 and 4,181,132 show implantable connectors which provide for percutaneous access to implanted shunts.

Related co-pending applications, assigned to the assignee of the present application, include Ser. Nos. 08/745,903; 08/724,948; 08/634,634; 08/539,105; and 60/036,124.

The full disclosures of each of the U.S. Patents and co-pending applications listed above are hereby incorporated herein by reference.

SUMMARY OF THE INVENTION

The present invention provides improved methods, systems, and kits for maintaining access to body lumens, particularly blood vessels, but also the peritoneal cavity, and the like. The systems comprise an access cannula, usually comprising a distal portion and a proximal portion, which is implanted from the body lumen to a proximal access site, typically an implanted port or a transcutaneous access location catheter. Distal access to the body lumen is effected by any one of a variety of access devices and techniques, such as in-dwelling cannulas, cross-tubes (T-catheters), end-to-side anastomosis, and the like. The methods and the systems of the present invention facilitate and simplify replacement of all or a portion of the systems implanted should such replacement become necessary.

According to the present invention, an implanted cannula system may be replaced by separately removing either a distal portion or a proximal portion thereof. The methods comprise surgically exposing a portion of the access cannula while leaving at least one of the distal end (attached to a body lumen) and the proximal portion unexposed. The access cannula is disconnected at the site where it has been exposed (typically by removing one end from a remote connector or severing the cannula at a pre-selected site along its length to produce a free end for subsequent reconnection) and thereafter replacing one of the distal portion and the proximal portion while leaving the other in place. The replaced section can then be connected to the previously implanted section in order to reestablish access. Typically, the entire distal end of the cannula will be exposed when it is desired to replace the distal portion. Alternatively, the entire proximal portion of the cannula may be exposed when it is desired to replace the proximal portion. Alternatively, when replacing the proximal portion which is connected at its proximal end to an implanted port, it may only be necessary to surgically expose the port and the distal end of the proximal portion leaving the intermediate portion thereof subcutaneously implanted.

The methods of the present invention for replacing portion(s) of a previously implanted cannula system will be useful where the implanted cannula comprises a proximal section and a separate distal section, typically connected by an intermediate connector, as described in more detail below. The methods will also be useful for replacing portions of an "integral" cannula, e.g., a cannula formed from a continuous tube without discrete connection points within the tube. When employed with two-piece cannulas (or optionally cannulas having three or more pieces), the replacement may be performed at a point of prior attachment, usually the point where the cannula is connected by the immediate connector(s). When employed with integral cannulas, it will be necessary to cut or otherwise sever the cannula at a point to which a new section of the cannula can be reattached. Of course, even when employing multiple-piece cannulas, it will be possible to sever the cannula body at other sites (i.e., where no connectors are present) to perform the replacement methods of the present invention.

Thus, in a first aspect of the method of the present invention, the distal end and the proximal portion of the implanted cannula are joined by a connector, typically a connector as described in detail below. The surgical exposing step comprises exposing the connector, and the disconnecting step comprises removing one of the distal end of the cannula or the proximal portion of the cannula from the connector. The reconnecting step comprises attaching at least a replacement distal end or a replacement proximal portion, depending on which components of the previously implanted cannula have been removed. Replacement may involve removing the previously implanted connector or not. If the previously implanted connector is removed, it will be necessary to provide and attach a new connector. If the previously implanted connector is not removed, the new section of the cannula may be attached directly to the previously implanted cannula.

In a second aspect of the method of the present invention, the distal end and the proximal portion of the implanted cannula are integrally formed, i.e., formed as a continuous tube without the use of discrete connectors as described elsewhere herein. With such integral cannulas, the disconnecting step comprises severing the continuous tube to produce a free implanted end, e.g., either a free proximal end of the distal end of the cannula or a free distal end of the proximal portion of the cannula. In either case, the reconnecting step comprises attaching a connector to the free implanted end of the continuous tube, and the attaching step comprises attaching a tubular replacement section to the connector. The tubular replacement section will either be a distal end of the cannula or a proximal portion of the cannula, depending on which implanted portion has been removed.

The connector preferably comprises a body having a first attachment aperture, a second attachment aperture, and an unobstructed flow lumen therethrough. Optionally, the first attachment aperture can branch into a plurality of additional attachment apertures so that a single proximal access cannula can be connected to a plurality of distal access cannulas, or vice versa. The flow lumen(s) through the body may be coaxial or parallel, but can also be curved or deflected so that the first attachment aperture and second attachment aperture define an angle therebetween, typically in the range from 45° to 270°, preferably in the range from 90° to 180°. Optionally, the lumen through the connector body may be flared, tapered, or stepped in one direction or the other in order to provide a transition from a small diameter at one end to a larger diameter at the other end.

The connecting step of the method for establishing body lumen access typically comprises providing an intermediate connector having a first attachment aperture for attaching a proximal end of the distal access cannula and a second attachment aperture for connecting a distal end of the proximal access cannula. While the respective ends of the distal and proximal access cannulas could be connected directly, e.g., one or both could have a connector mounted thereon, it is preferable to provide an intermediate connector which is capable of attaching a "bare" tube. In this way, the access cannulas may be cut to their desired lengths, and the resulting "bare" cut end attached to the intermediate connector in a convenient manner, typically by placing over an end of the connector and tying using suture or other filament.

The intermediate connectors may be linear, i.e., with a straight lumen so that the distal and proximal access cannulas are coaxially aligned at their point of attachment. Alternatively, the connectors can be non-linear, e.g., with their first and second attachment apertures disposed at a relative angle in the range from 45° to 270°, preferably from 90° to 180°, in order to dispose the distal and proximal access cannulas in a non-linear fashion.

In a particularly preferred aspect of the present invention, the remote connectors may be adapted to connect a large diameter proximal access cannula to a smaller diameter distal access cannula. In some cases, the connector itself may provide for a transition in the lumen diameter connecting the two cannulas, but such a transition is not necessary, and the change of diameter may be provided within one of the cannulas, preferably the distal access cannula. Such connectors are particularly useful for providing the low flow resistance access cannulas described above.

The present invention further comprises kits including at least one of the system components which may be replaced according to the methods of the present invention, e.g., a proximal cannula portion, a distal cannula end, and/or a connector adapted to connect a proximal cannula portion to a distal cannula end. The kits will further comprise instructions for use setting forth any of the methods of the present invention as described above. Usually, at least some of the system components and/or instructions for use will be packaged in conventional medical device packaging, such as a box, pouch, tray, tube, or the like. The instructions may be printed on a package insert (typically a separate sheet within the packaging) and/or may be printed in whole or in part on a portion of the packaging. Usually, at least some of the system components will be maintained sterilely within the packaging.

DESCRIPTION OF THE SPECIFIC EMBODIMENTS

Figure 1:
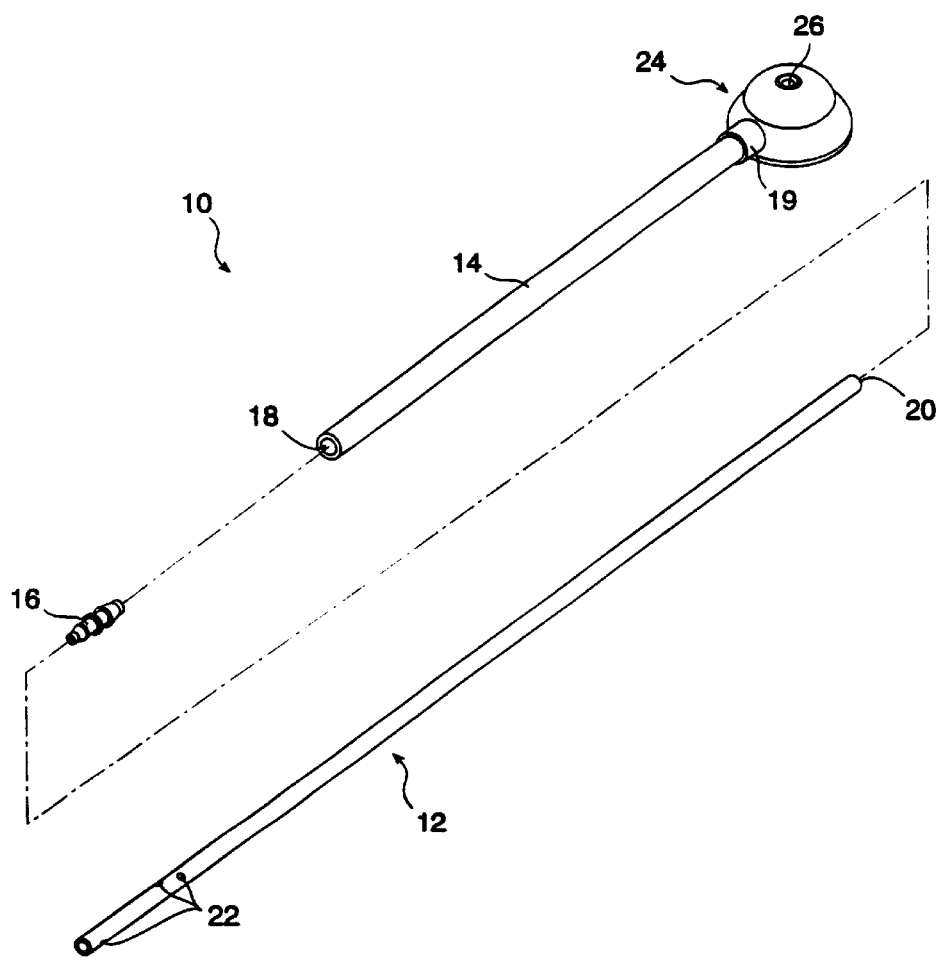
FIG. 1 is an isometric view of a first embodiment of a body lumen access system constructed in accordance with the principles of the present invention and comprising an in-dwelling venous cannula, an implantable port having a proximal access cannula attached thereto, and a connector for connecting the proximal access cannula to the in-dwelling venous cannula.

The present invention provides methods and apparatus for facilitating and maintaining percutaneous and transcutaneous access to a body lumen of a patient. Exemplary body lumens, include blood vessels, the peritoneal cavity, and the like. The methods are particularly useful for accessing blood vessels, including both arterial blood vessels and venous blood vessels. While the remaining description is directed particularly at blood vessels, it will be appreciated that the invention applies to all body lumens and cavities where selective percutaneous access might be desired.

For percutaneous access, ports are implanted subcutaneously so that a passage therein lies a short distance beneath the surface of the patient's skin, typically being within 3 mm to 20 mm of the skin's surface. An access tube may then be percutaneously inserted into the passage in the access port in order to provide a connection to the blood vessel via the access port. For transcutaneous access, a catheter (usually defining a proximal access cannula according to the present invention) is implanted through the patient's skin with a proximal end of the catheter adapted for connection to an external catheter. In both cases, access can be provided for a variety of purposes, usually involving withdrawal of blood, the extracorporeal treatment of the withdrawn blood, and/or the return of the treated blood to the patient. Such extracorporeal blood treatment will most often be for hemodialysis, but can also be for hemofiltration, hemodiafiltration, apheresis, and the like. In addition to extracorporeal treatment, the access port of the present invention can be used for perfusing drugs, fluids, and other materials directly into a patient's circulation for a variety of purposes.

Apparatus according to the present invention will comprise access cannulas, usually but not necessarily including both a distal access cannula which is connected to or implanted within the body lumen and a separate proximal access cannula which is connected to an implanted port or transcutaneously positioned through the patient's skin. A proximal end of the distal access cannula is connected or connectable to a distal end of the proximal access cannula at a subcutaneous junction region, typically by a connector. The cannulas will typically comprise polymeric tubes extruded from conventional, biocompatible catheter materials, such as silicone rubber, polyurethane, and the like. The distal access cannula will typically have a low profile, particularly when all or a distal portion thereof is intended for implantation in a venous lumen. Exemplary distal catheters will have a length in the range from 5 cm to 45 cm, usually from 10 cm to 30 cm, an outer diameter in the range from 2 mm to 8 mm, usually from 3 mm to 6 mm, and a lumen diameter in the range from 1 mm to 6 mm, usually from 2 mm to 5 mm. The proximal access cannula will have a length in the range from 3 cm to 45 cm, usually from 5 cm to 15 cm, an outer diameter in the range from 4 mm to 11 mm, usually from 6 mm to 8 mm, and a lumen diameter in the range from 3 mm to 10 mm, usually from 5 mm to 7 mm. The access cannulas will usually be tubes having uniform diameters along their entire lengths, but may have tapered, stepped, or other variations in diameter, as described previously. The distal end of the proximal access cannula and proximal end of the distal access cannula will usually be uniform over a length sufficient to permit cutting, where the cut end of the cannula will have identical diameter and other properties so that the cut end may fit over an attachment aperture on the remote connector, as described in more detail below.

As described above, the access cannula comprises at least a discrete distal portion and a discrete proximal portion, where the portions are separate and connectable through a connector. In another aspect of the apparatus of the present invention, the distal and proximal portions of the access cannula may be formed integrally with the distal portion having a reduced diameter and the proximal portion having an enlarged diameter to reduce the overall flow resistance presented by the access cannula. The lengths of such catheters can be adjusted by cutting at either the proximal end or the distal end, but the transition region where the diameter changes will generally be integrally formed and unavailable for cutting.

Referring now to FIG. 1, an access system 10 according to the present invention comprises a distal access cannula 12, a proximal access cannula 14, and a connector 16 adapted for connecting a distal end 18 of the proximal access cannula to a proximal end 20 of the distal access cannula. The distal access cannula 12 is in the form of an in-dwelling venous catheter and includes a plurality of apertures 22 near its distal end to increase blood inflow or outflow through the cannula. The outer diameter of the venous access cannula 12 (as least over a distal portion thereof and usually over its entire length) will typically be in the range from 2 mm to 8 mm, preferably from 3 mm to 6 mm, and the luminal diameter will be in the range from 1 mm to 6 mm, preferably from 2 mm to 5 mm.

An implantable port 24 is secured to a proximal end 19 of the proximal access cannula 14. The port 24 can be integrally or removably secured to the end 19, both of which are described in co-pending application Ser. No. 60/036,124, the full disclosure of which has been previously incorporated herein by reference. The port 24 provides for percutaneous access to the access system 10 by means of a needle or other access tube which is introduced through the patient's skin into an orifice 26 at the top of the port. Implantation of the access system 10 will be described in more detail in connection with FIGS. 11A and 11B below.

Figure 14:
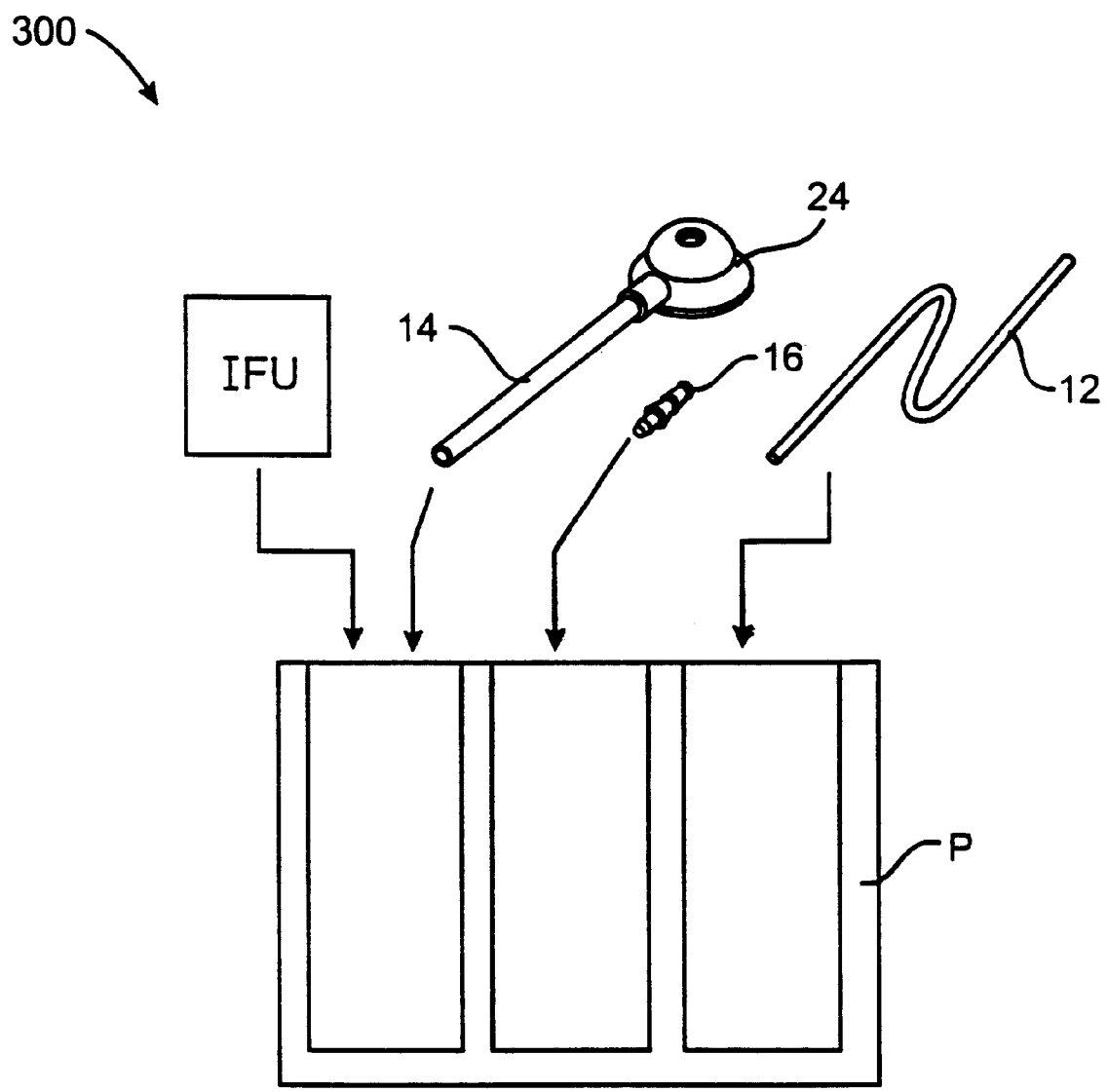
FIG. 14 illustrates a kit according to the present invention comprising cannula replacement components together with instructions for use (IFU) and a package.

The system 10 of FIG. 1, or any of the other systems and individual components thereof, may be packaged together with instructions for use (IFU), as shown in FIG. 14. A conventional package, which may be a pouch P or any other suitable package, such as a tray, box, tube, or the like, contains the system 10 with the different components being optionally held in different, isolated pockets 200, 202, and 204 in the pouch P. Usually, the system 10 will be sterilized within the package, e.g., by radiation or ethylene oxide, and the instructions are provided on either the package itself or a separate printed sheet. The instructions will set forth any of the aspects of the method of the present invention described herein.

Figure 1A:
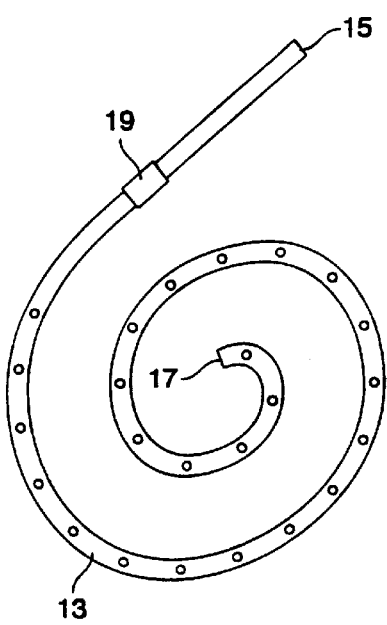

Referring now to FIG. 1A, the system 10 may be modified for use in peritoneal dialysis by substituting a pig-tail catheter 13 for the distal access cannula 12. The pig-tail catheter has a proximal end 15 adapted to be connected to the connector 16 and a distal end 17 which is similar in design to a conventional peritoneal dialysis catheter. The catheter 13 includes a cuff 19 which is implanted in the peritoneal wall, and the proximal end can be trimmed to join the connector 16 in the same manner as described below for vascular access.

Figure 2:
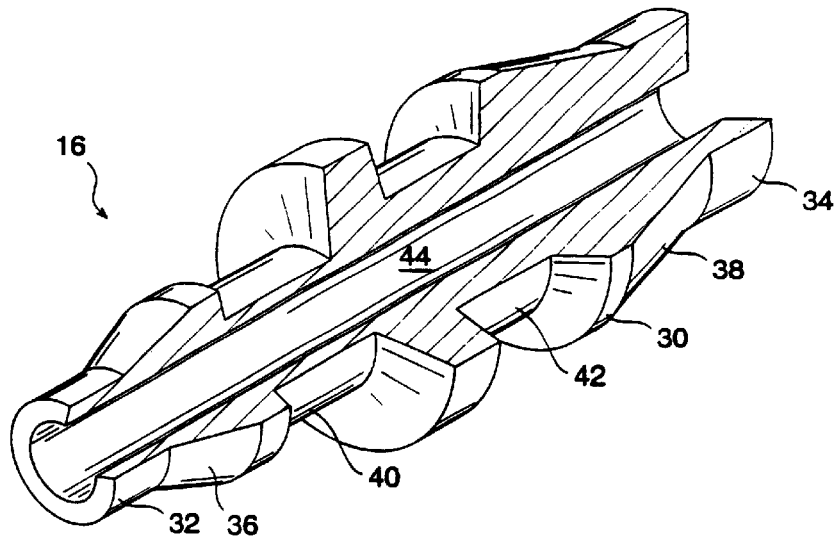
FIG. 2 is a detailed view of the connector of FIG. 1, shown in section.

Referring now to FIG. 2, the connector 16 comprises a body 30, typically composed of a biocompatible metal or thermoplastic, such as titanium. The connector body 30 defines a first attachment aperture 32, typically having a relatively small diameter to receive the proximal end 20 of the distal access cannula 12 (where the end 20 may be cut or trimmed prior to connection), and a large diameter connection aperture 34 adapted to receive the distal end 18 of the proximal access cannula 14 (which also may be cut or trimmed prior to connection). Each attachment aperture 32 and 34 has a conical portion 36 and 38, respectively, and a reduced diameter region 40 and 42, respectively, to facilitate attachment of the tubular ends of the access cannulas. In particular, the tubular ends, which are typically silicone rubber or other elastomeric material, are pushed over the conical region and into the reduced diameter region. Thereafter, the ends of the cannulas can be tied to the reduced diameter region using suture or other biocompatible material. A lumen 44 through the connector body 30 can have a uniform diameter along its entire length, usually from 1 mm to 10 mm, or can be tapered to increase in diameter toward the larger attachment aperture 34 intended to connect to the proximal access cannula 14.

Figure 3:
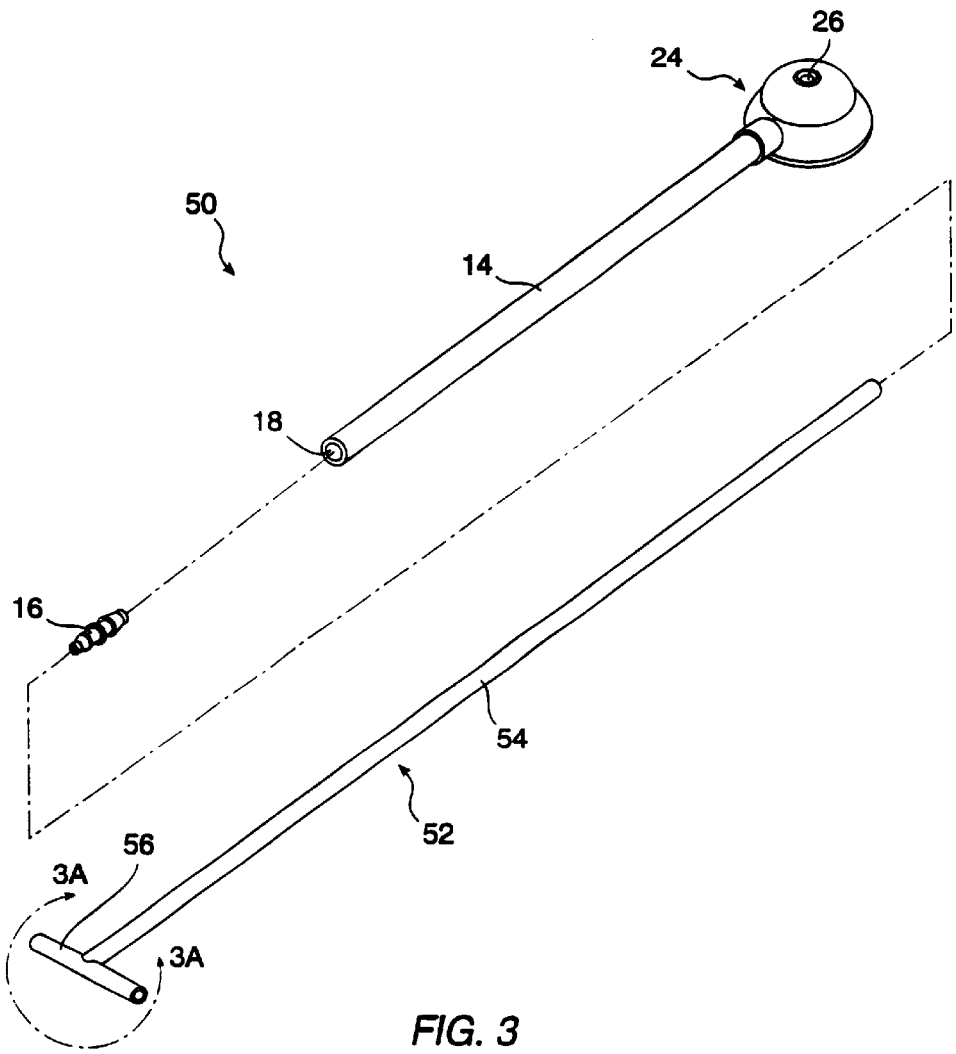
FIG. 3 is an isometric view of a second embodiment of a body lumen access system constructed in accordance with the principles of the present invention and comprising a distal access cannula having a cross-tube at its distal end, an implantable port having a proximal access cannula attached thereto, and a connector for connecting the distal access cannula to the proximal access cannula.
Figure 3A:
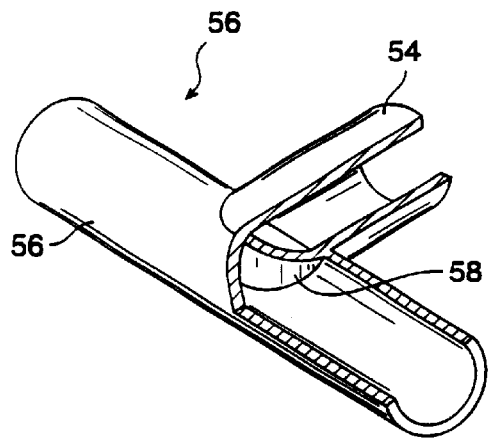
FIG. 3A is a detailed view of the distal end of the distal access cannula of FIG. 3.

Referring now to FIG. 3, a second access system 50 constructed in accordance with the principles of the present invention comprises a proximal access cannula 14 and connector 16, generally as described above in connection with the embodiment of FIG. 1. A distal access cannula 52 generally comprises an axial tubular body 54 having the dimensions generally set forth above, but terminating at its distal end in a cross-tube 56 as best illustrated in FIG. 3A. The cross-tube is in the form of a T-catheter, described in detail in co-pending applications Ser. Nos. 08/539,105 and 08/724,948, the full disclosures of which are incorporated herein by reference. The cross-tube 56 is intended for implantation within the lumen of a blood vessel in a minimally intrusive manner. A valve 58, typically a slit valve, is provided at the distal end of the tube 54 to inhibit blood flow into the lumen of tube 54 in the absence of a differential pressure. Thus, blood flow into the tube will be prevented unless there is a positive or negative pressure applied through the port 24 in order to effect the inflow or outflow of blood.

Figure 4:
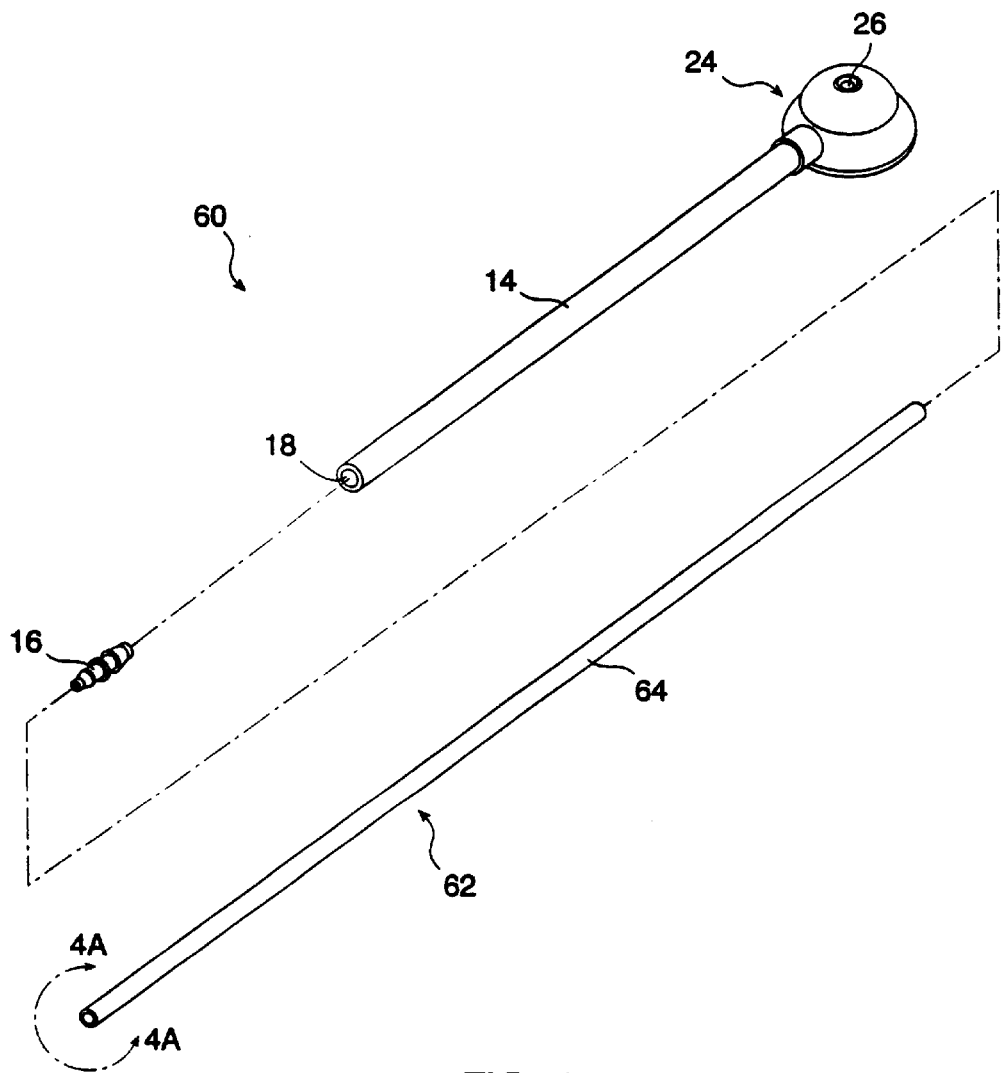
FIG. 4 is an isometric view of a third embodiment of a body lumen access system constructed in accordance with the principles of the present invention and comprising a distal access cannula having a distal end adapted for connection to a body lumen by an anastomosis, an implantable port having a proximal access cannula attached thereto, and a connector for connecting the distal access cannula to the proximal access cannula.
Figure 4A:
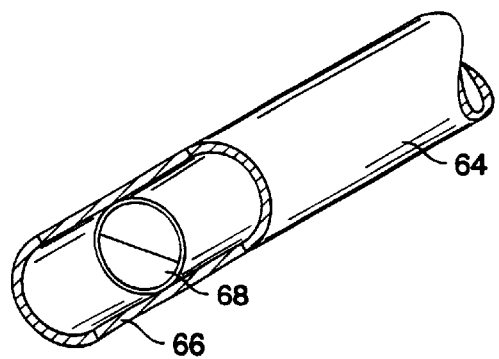
FIG. 4A is a detailed view of the distal end of the distal access cannula of FIG. 4.

A third access system 60 constructed in accordance with the principles of the present invention is illustrated in FIG. 4. Access system 60 comprises a proximal access cannula 14 and connector 16, generally as described above in connection with FIG. 1. Distal access cannula 62 comprises a tubular member 64 terminating at its distal end in a suturing cuff 66, generally as illustrated in FIG. 4A. A membrane 68 having a slit valve therein is provided to prevent flow into or out of the lumen of tube 64 in the absence of a differential pressure. Suturing of the distal access cannula 64 to a blood vessel or other body lumen is described in U.S. Pat. No. 5,562,617, the full disclosure of which has previously been incorporated herein by reference.

Figure 5:
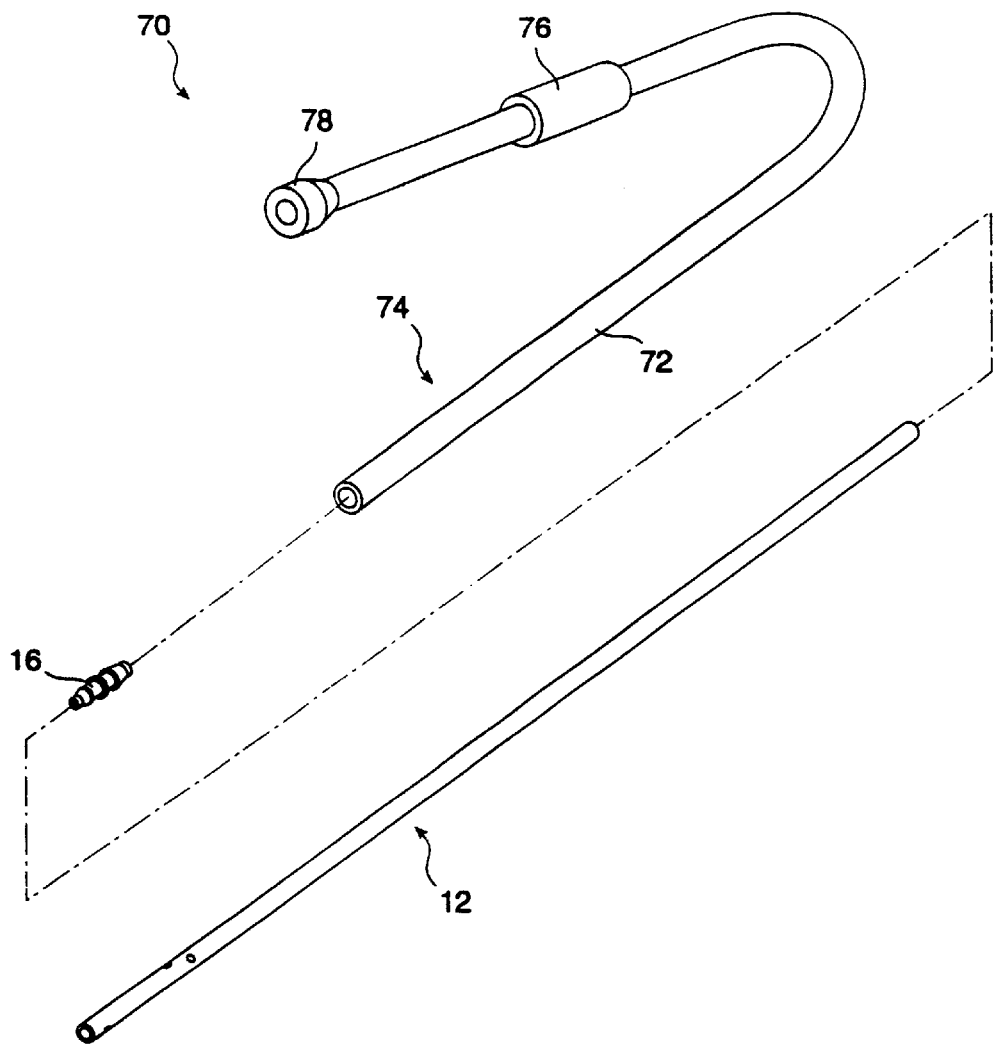
FIG. 5 is an isometric view of a fourth embodiment of a body lumen access system constructed in accordance with the principles of the present invention and comprising an in-dwelling venous cannula, a transcutaneous proximal access cannula, and a connector for connecting the in-dwelling venous cannula to the transcutaneous proximal access cannula.

A fourth access system 70 constructed in accordance with the principles of the present invention is illustrated in FIG. 5. The access system 70 comprises a distal access cannula 12 and connector 16, generally as described above in connection with FIG. 1. A proximal access cannula 72 is intended for transcutaneous placement through a patient's skin, as described in more detail in connection with FIG. 12 below. The proximal access cannula will comprise a distal end 74 which may be trimmed for connection to the connector 16. The proximal access cannula 72 will preferably comprise a cuff 76 which is intended to be implanted immediately beneath the patients skin and to inhibit bacterial contamination through the cannula, as is generally known for venous in-dwelling catheters. A standard luer or other connector 78 will be provided at the proximal end of the access cannula 72 to permit connection to an external catheter.

Figure 6:
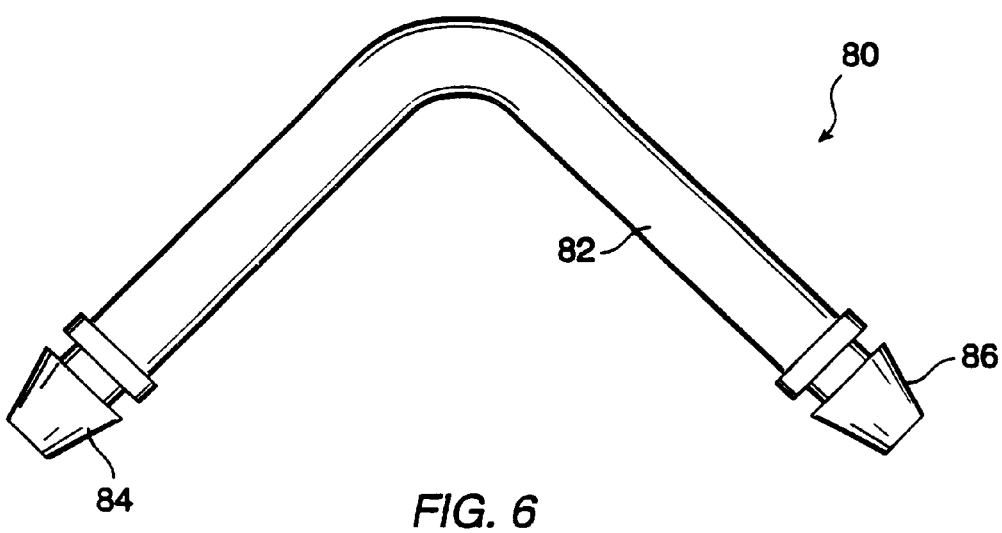
FIG. 6 illustrates a connector having a 90° bend.
Figure 7:
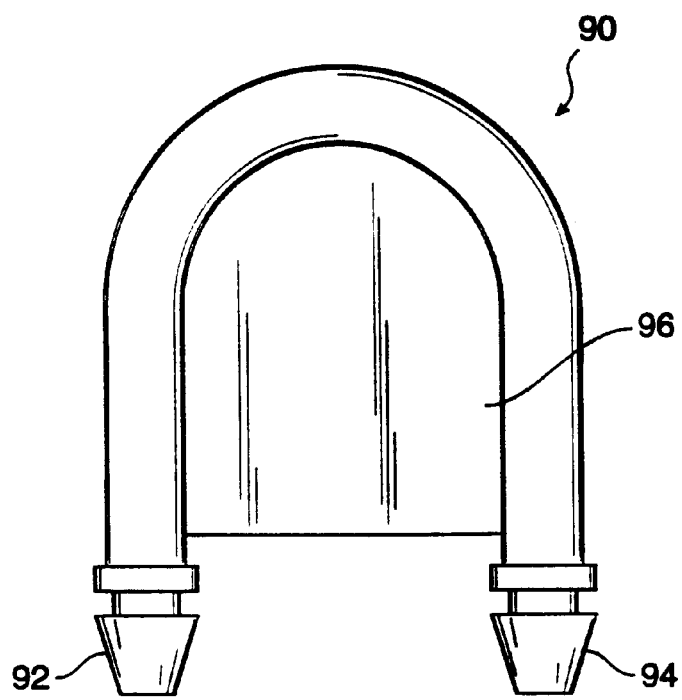
FIG. 7 illustrates a connector having a 180° bend.

The connector 16 provides a linear attachment of the distal access cannula to the proximal access cannula. In many cases, it will be desirable to provide a non-linear connection to facilitate positioning of the remote access site relative to the body lumen access site. A connector 80 which provides for a 90° relative angle between the distal and proximal access cannulas is illustrated in FIG. 6. The connector 80 comprises a bent tube 82 having a first attachment aperture 84 and a second attachment 86. As illustrated, the attachment apertures are identical, but they could easily have different sizes intended for attaching to a larger proximal access cannula and a smaller distal access cannula. A second bent connector 90 is illustrated in FIG. 7. Connector 90 is U-shaped and provides for a 180° turn between attachment aperture 92 and attachment aperture 94. Again, the attachment apertures 92 and 94 are illustrated as having the same size, but will frequently different sizes intended to attach different sized cannulas. The connector 90 also includes a web 96 spanning the region between adjacent legs of the connector. The web 96 is intended to prevent tissue ingrowth around the connector, thus facilitating removal should that become necessary. The web 96 also provides a relatively large target for a surgeon attempting to access the connector for replacement of either cannula, with or without replacement of the connector. Without such a connector, there is significant risk that the surgeon attempting to access the subcutaneous junction region where the connector is positioned will accidentally cut or otherwise damage one of the cannulas which are composed of a silicone material which can easily be cut.

Figure 8:
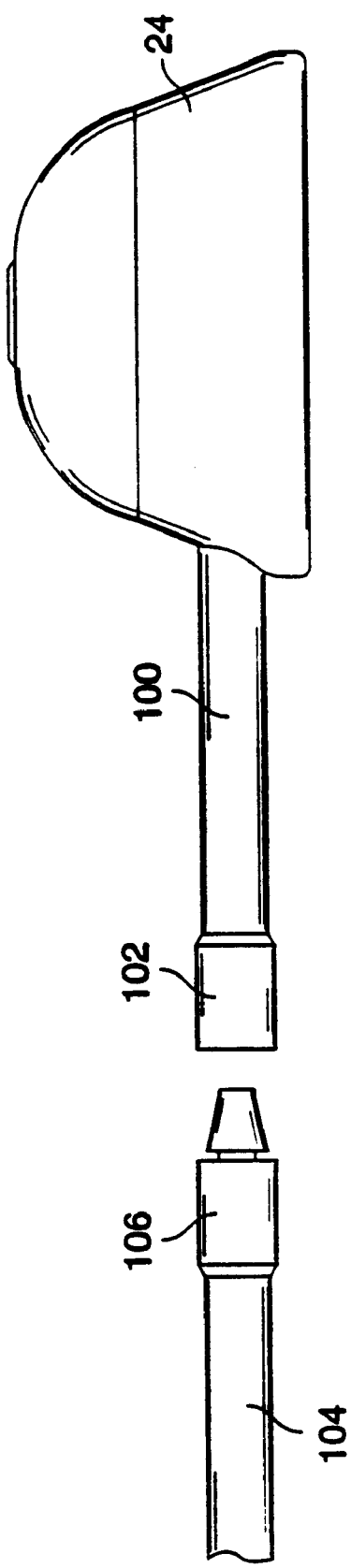
FIG. 8 illustrates an implantable port having an integral proximal cannula and a distal access cannula, wherein both the proximal cannula and the distal cannula have integral connectors thereon.

A less preferred access system according to the present invention is illustrated in FIG. 8. This system is described in co-pending parent application Ser. No. 60/036,124, the full disclosure of which has previously been incorporated herein by reference. Implantable port 24 comprises an integral proximal access cannula 100 having an integral connector 102 at its distal end. A distal access cannula 104, which may be in any of the forms described above, comprises an integral connector 106 at its proximal end, where the connectors 102 and 106 are intended for mating. While the assembly illustrate in FIG. 8 provides many of the advantages described herein above, such as the ability to provide for a larger lumen diameter in the proximal access cannula 100 and the ability to separately remove and replace either the proximal access cannula (together with the port 24) or the distal access cannula 104, it lacks many of the other advantages described above. In particular, by providing permanently affixed connectors 102 and 106, it is not possible to trim the ends of the cannulas which need to be connected. Also, the integral connection of the proximal access cannula 100 to the port 24 would prevent separate replacement of those two components.

Figure 9:
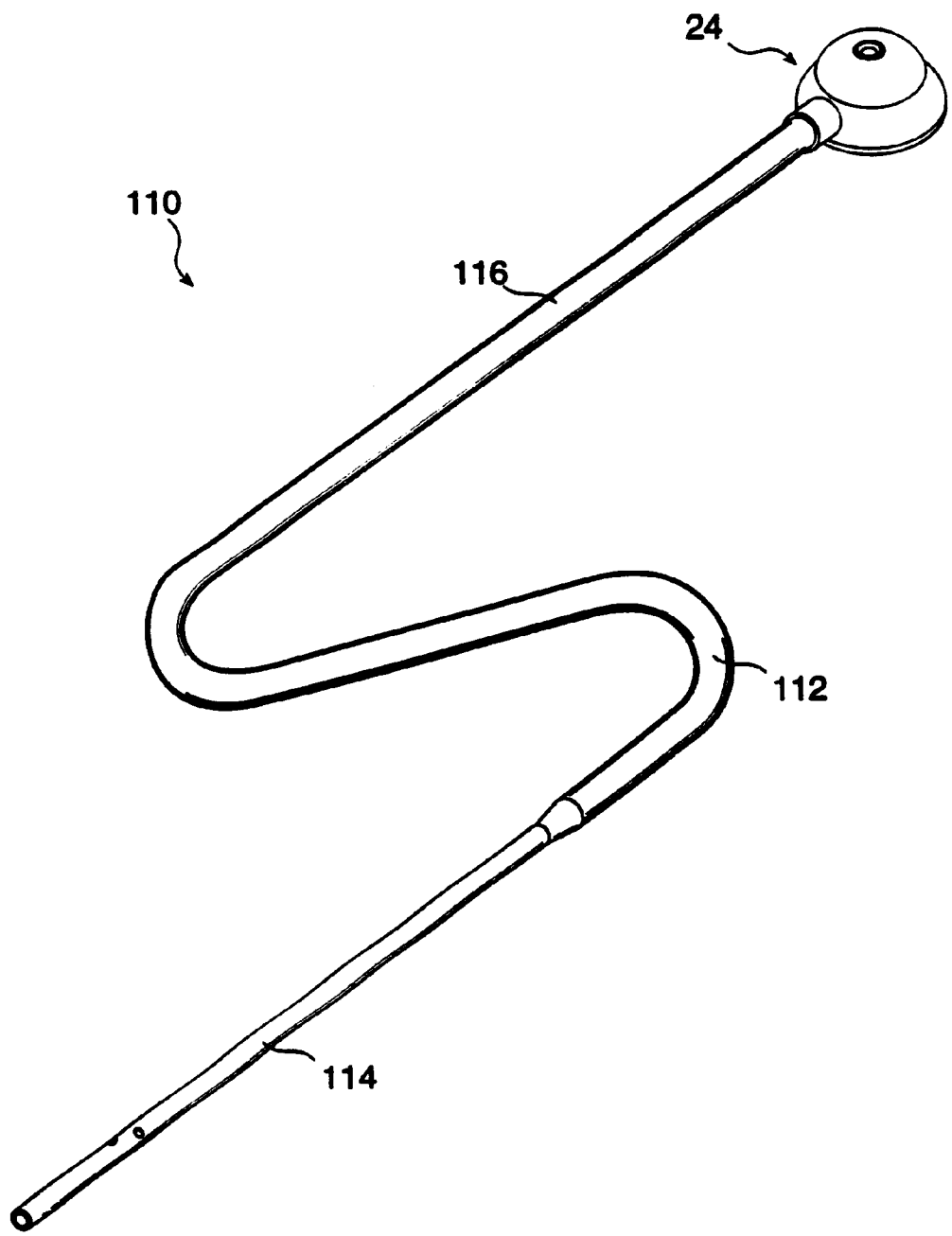
FIG. 9 illustrates a single-piece access cannula having a small diameter distal end and a large diameter proximal end, wherein the proximal end of the proximal portion of the cannula is attached or attachable to an implantable port.

Referring now to FIG. 9, a sixth access system 110 constructed in accordance with the principles of the present invention comprises a single-piece access cannula 112 having a small diameter distal portion 114 and a large diameter proximal portion 116. The proximal end of the proximal portion 116 is connected to an implantable port 24, generally as described above, but could also be fashioned as a transcutaneous catheter. The distal portion 114 of the access cannula 112 is shown as an in-dwelling catheter, but could be fashioned as any of the other distal cannulae described above, including the cross-tube configuration and the suturing cuff configuration. The access system 110 will have the advantages of the present invention with regard to reduced flow resistance, but is less preferred since it will not have the ability for improved implantation and improved replacement as described in more detail below.

Figure 10:
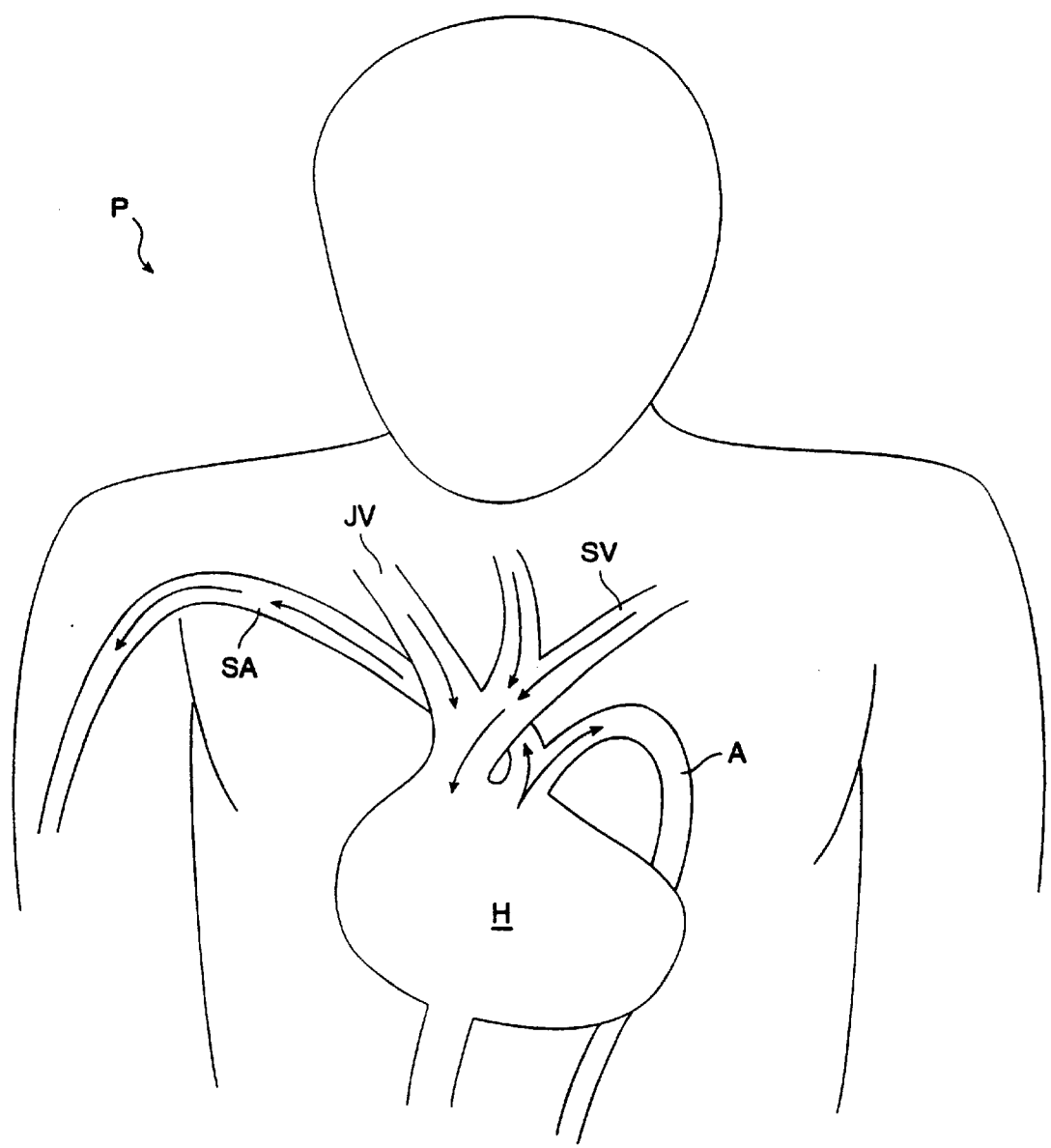
FIG. 10 illustrates patient vasculature to which the implantable access systems of the present invention can be connected.

The body lumen access systems described above are particularly suitable for establishing percutaneous and transcutaneous access to single or multiple locations in the patient's vasculature, including both the arterial and venous vasculature. As illustrated in FIG. 10, the arterial and venous vasculature of patient P in the region immediately surrounding the heart H includes the jugular vein JV, the subclavian vein SV, the subclavian artery SA, and the aorta A.

Figure 11A:
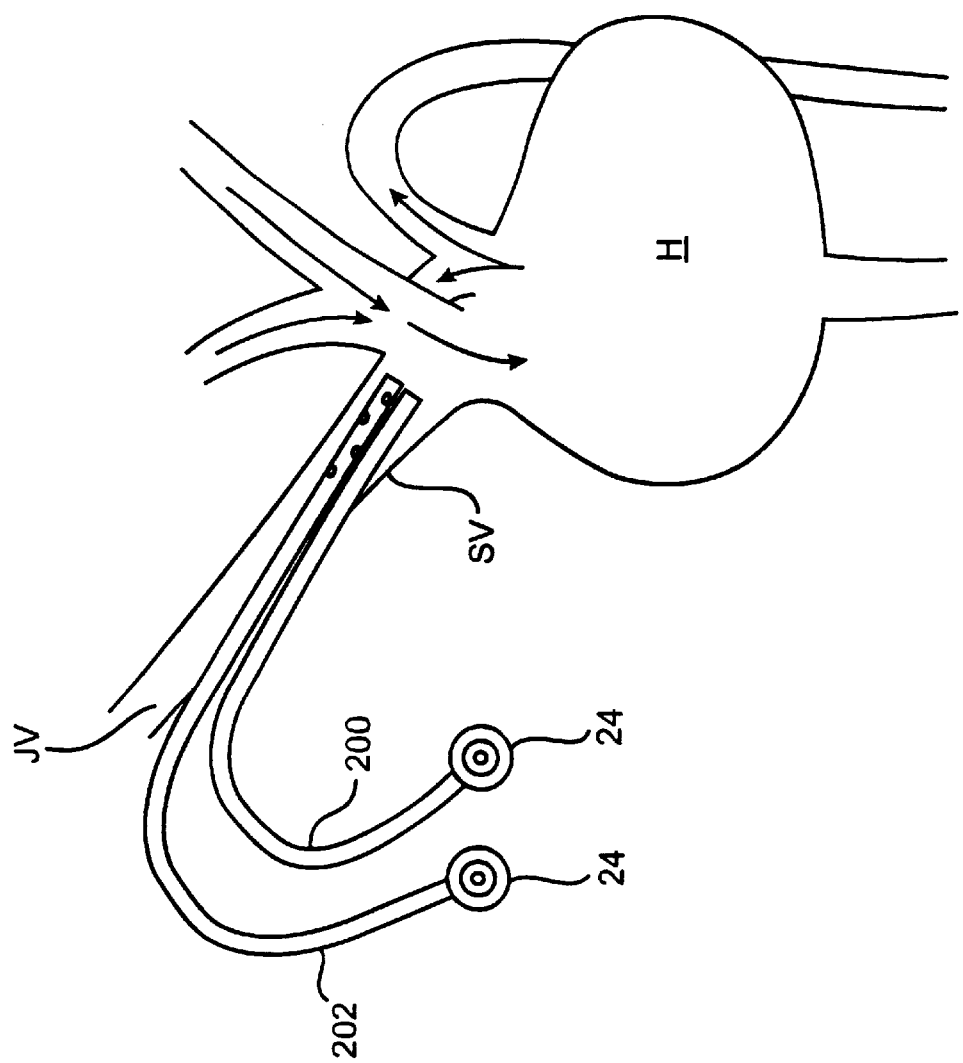
FIGS. 11A–11D illustrate a first cannula replacement protocol according to the methods of the present invention.
Figure 11B:
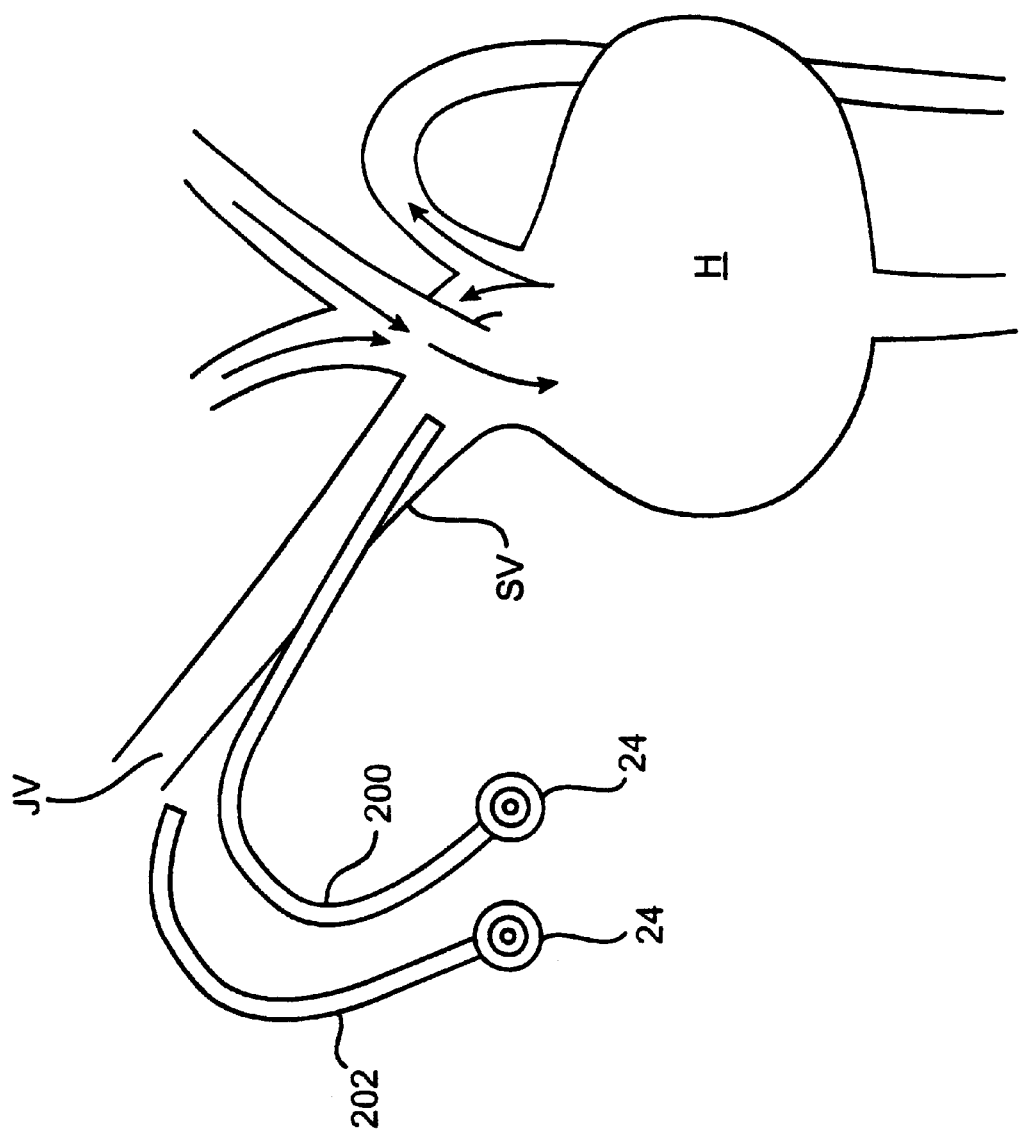

Referring now to FIG. 11A, the first exemplary replacement protocol according to the methods of the present invention will be described. A pair of implanted cannulas 200 and 202 extend between implanted ports 24 and subclavian vein SV. Both the cannulas 200 and 202 are formed from continuous tubular bodies so that no connectors, seams, or other discontinuities are present. The cannula 202 will have become dysfunctional for some reason, such as cannula malposition, infection, thrombosis, fibrin sheathing, or the like. Only the distal end of the cannula, however, is dysfunctional and needs to be replaced. The replacement procedure comprises first locating the cannula using conventional imaging techniques, such as fluoroscopy or conventional X-ray. Preferably, a relatively straight portion of the cannula is identified and is surgically exposed. Access will be achieved in conventional ways, typically a surgical cut down made in the axial direction of the cannula at the point at which it is to be replaced. After the cannula is exposed, a portion will be pulled partially out of the surgical incision, typically using a clamp. The cannula body is then cut proximal to the clamp, holding the proximal end of the distal end of the cannula so that it will not be lost into the vein. A second clamp is then used to grasp the proximal end of the distal section, leaving an opening to introduce a guidewire through the distal end. After introducing the guidewire, the cut section of the cannula may be removed over the wire, leaving a free implanted end of the cannula 202, as shown in FIG. 11B.

Figure 11C:
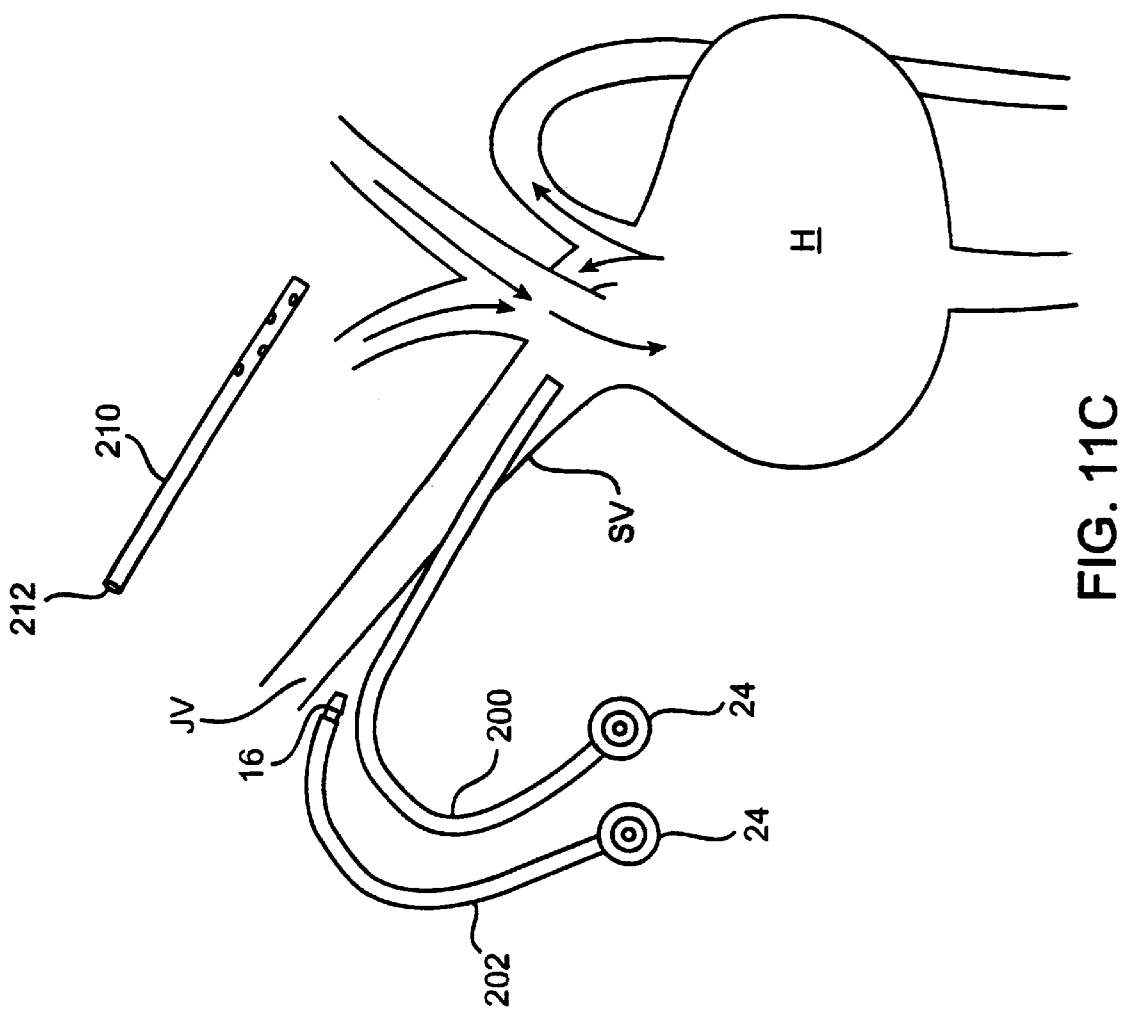
Figure 11D:
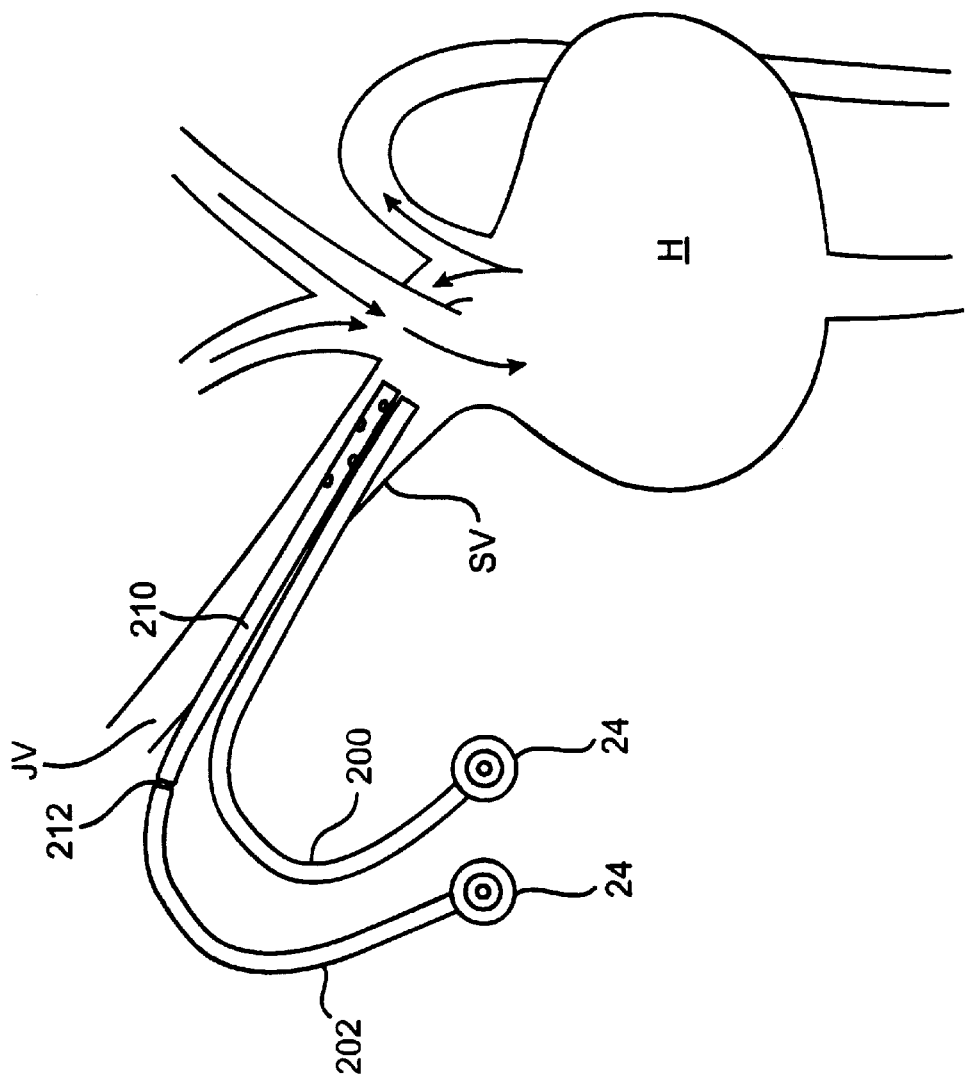

A replacement section 210 (FIG. 11C) for the cannula 202 is provided, typically being cut to length at end 212 so that it will have the proper length when reconnected to the proximal portion of the cannula. The replacement section 210 may be attached to the distal end of proximal portion, typically using a remote connector 16 as described previously. The end with side holes (uncut) is placed in the vein, and the cannula primed with saline to wet the surfaces. Using dry gauze to grip the cannula, the cannula is pushed over one end of the remote connector. The cannula is introduced over the guidewire to ensure that it is not lost in the vein. After the tip of the replacement section 210 is located properly, the guidewire may be removed and the replacement section connected to the remote connector 16. The cannula and remote connector are then lowered back into the incision, with the position of the distal cannula tip verified by imaging. The integrity of the repaired cannula 202 may then be tested by drawing blood through the associated port 24 and flushing the port with saline. Usually, a heparin lock will be introduced to the port. The cannula 202 having the replacement end 210 attached thereto is illustrated in FIG. 11D.

Figure 12A:
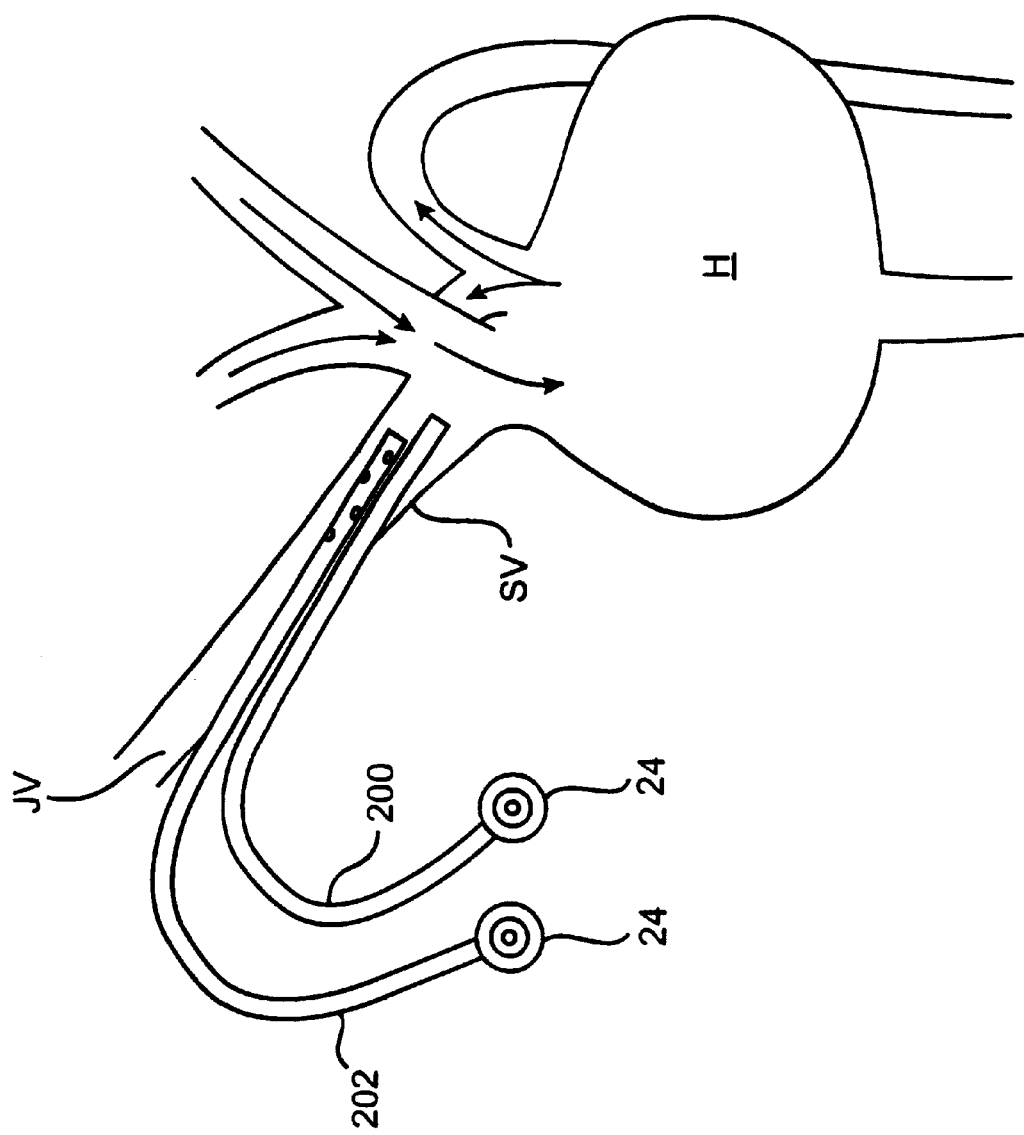
FIGS. 12A–12D illustrate a second cannula replacement protocol according to the methods of the present invention.
Figure 12B:
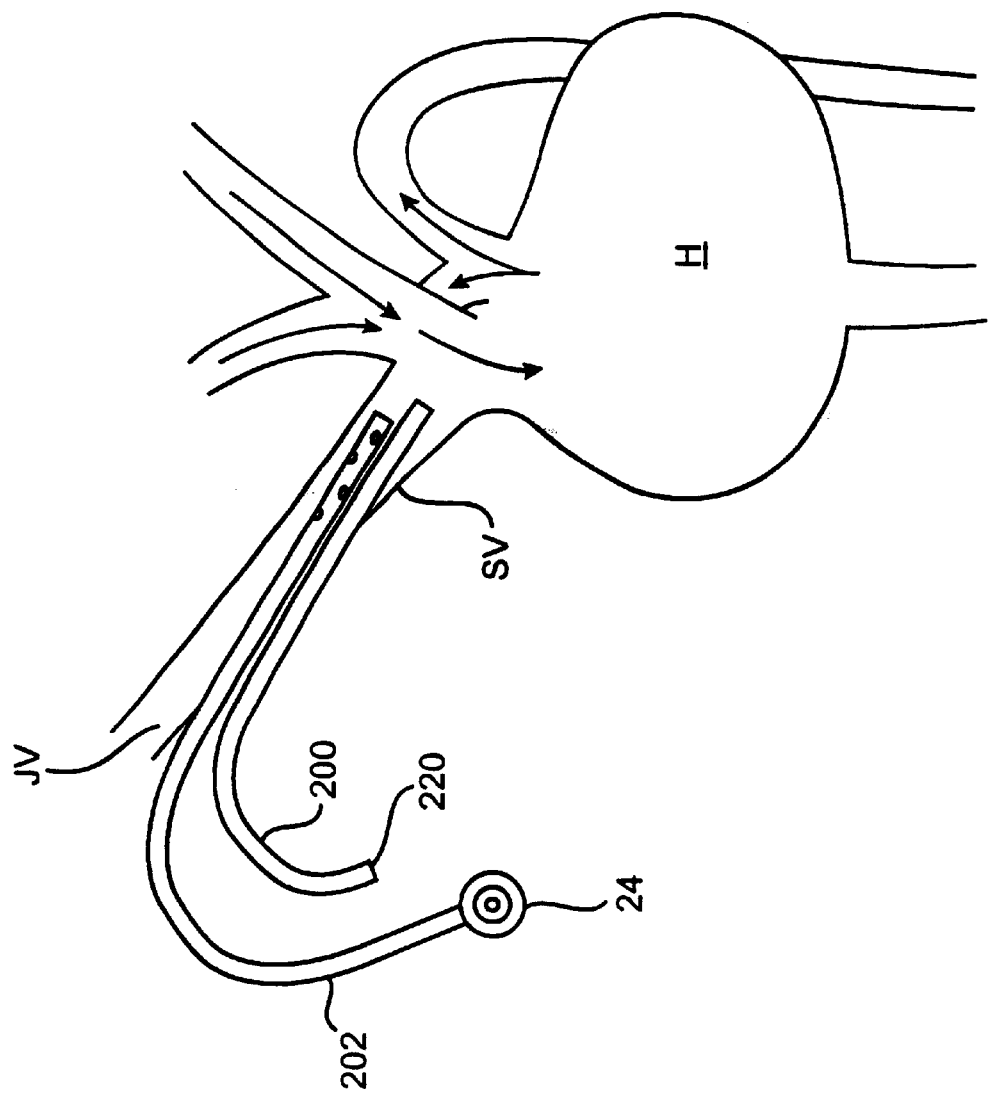
Figure 12C:
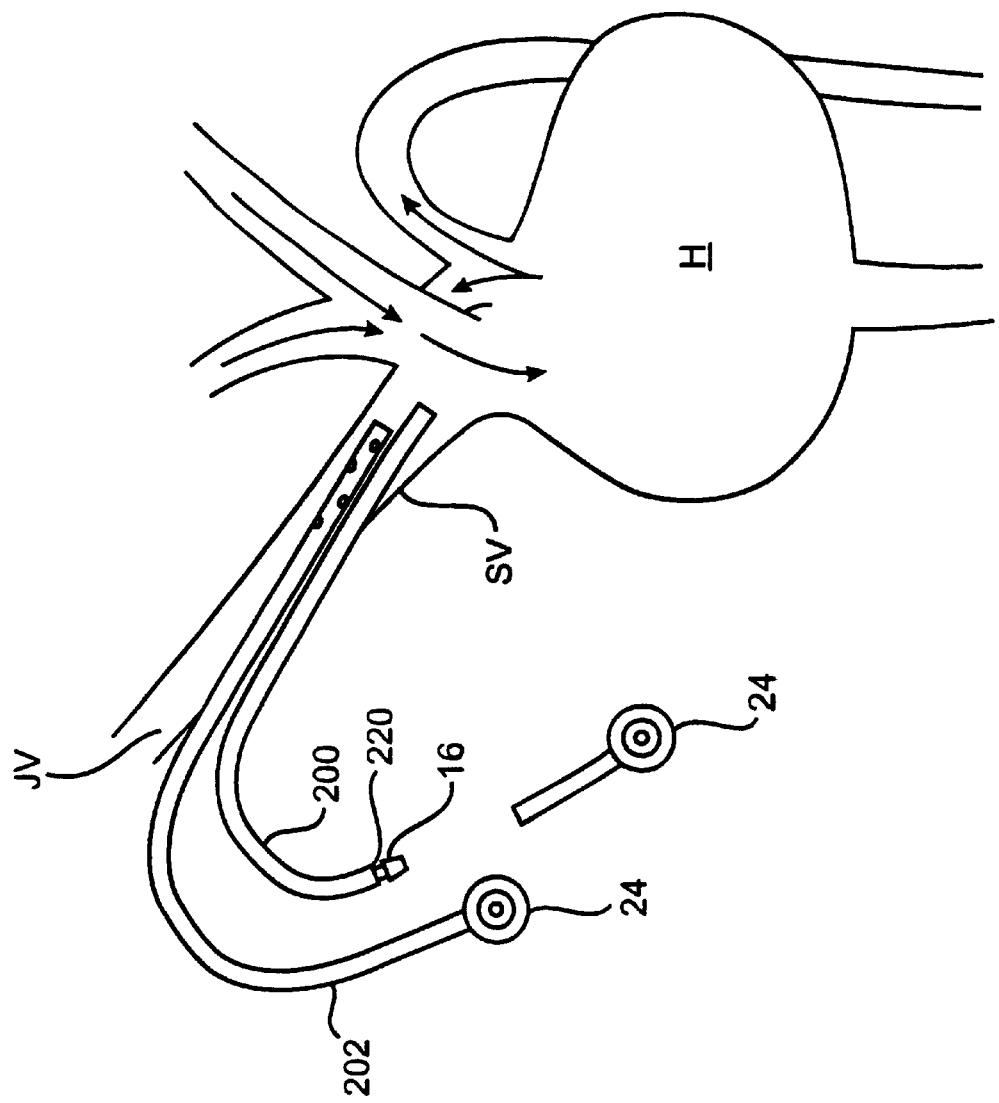
Figure 12D:
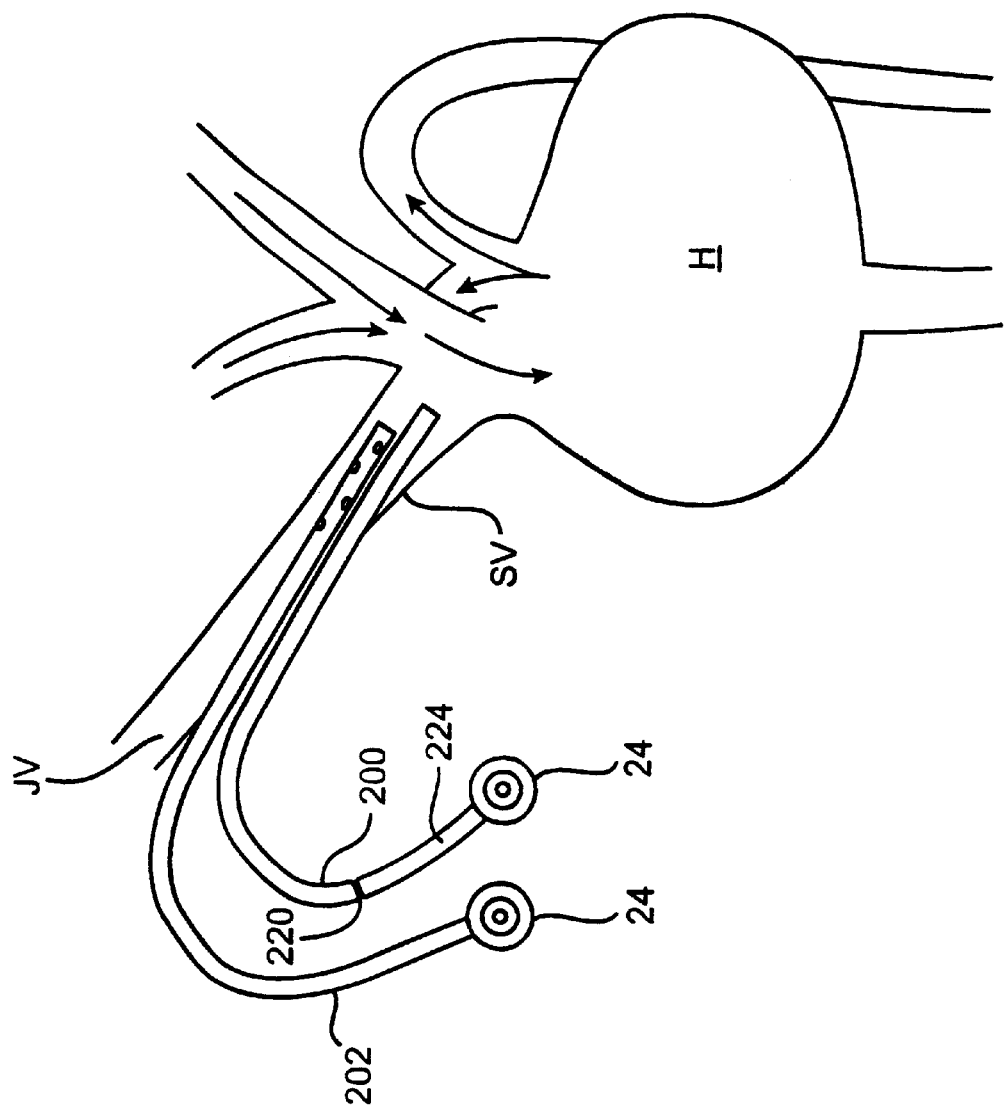

Referring now to FIGS. 12A–12D, replacement of the proximal portion of an implanted cannula 200 will be described. The proximal portion of cannula 200 is surgically accessed, typically under imaging as described previously. The location in the cannula 200 downstream from port 24 is identified and cut, leaving a pre-implanted end 220 on the cannula, as illustrated in FIG. 12B. A remote connector 16 may be introduced into the free end 220, as shown in FIG. 12C, and a replacement proximal portion 224 having a replacement valve 24 provided. The replacement proximal portion 224 may then be connected to the remote connector so that the cannula 220 is reconstructed, as shown in FIG. 12D.

Figure 13A:
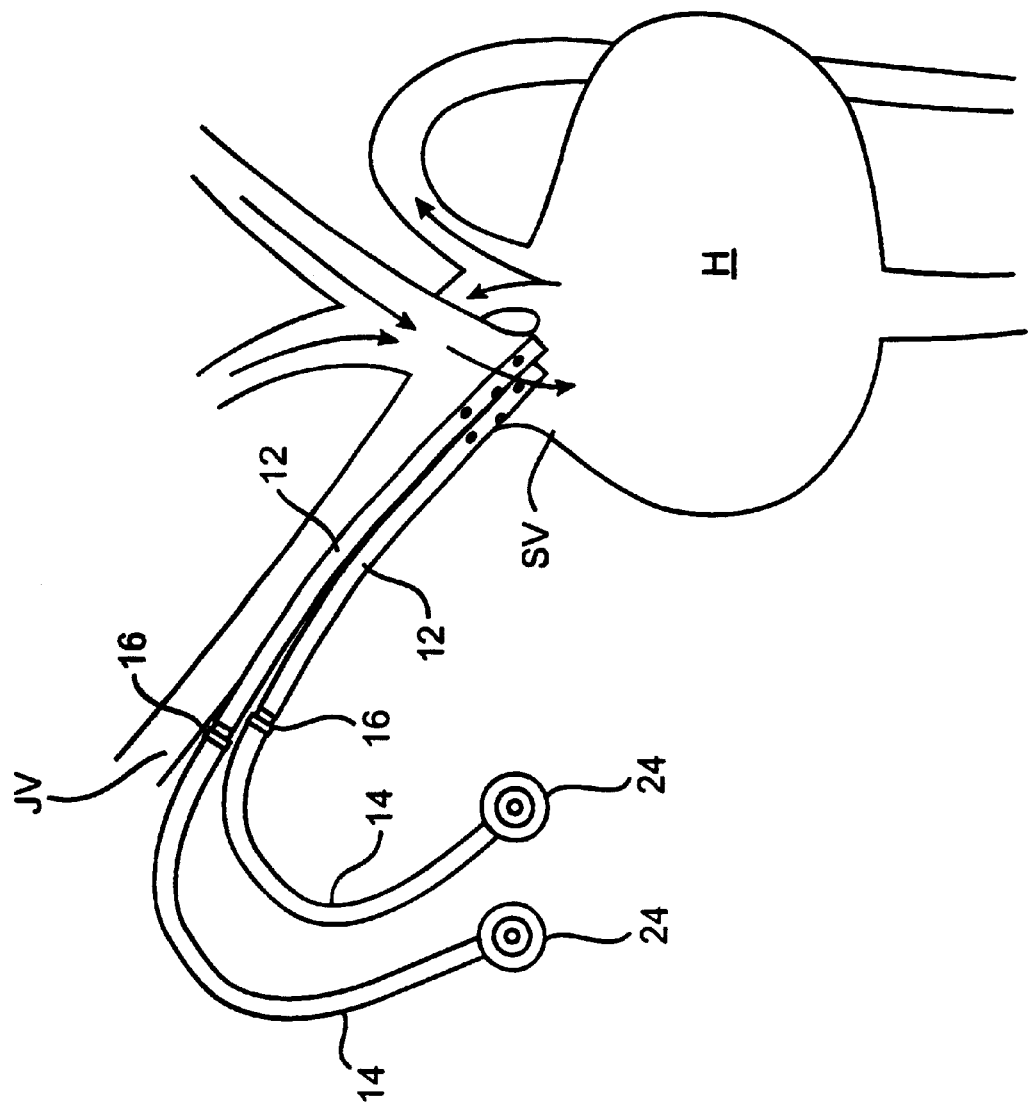
FIGS. 13A–13C illustrate a third cannula replacement protocol according to the methods of the present invention.
Figure 13B:
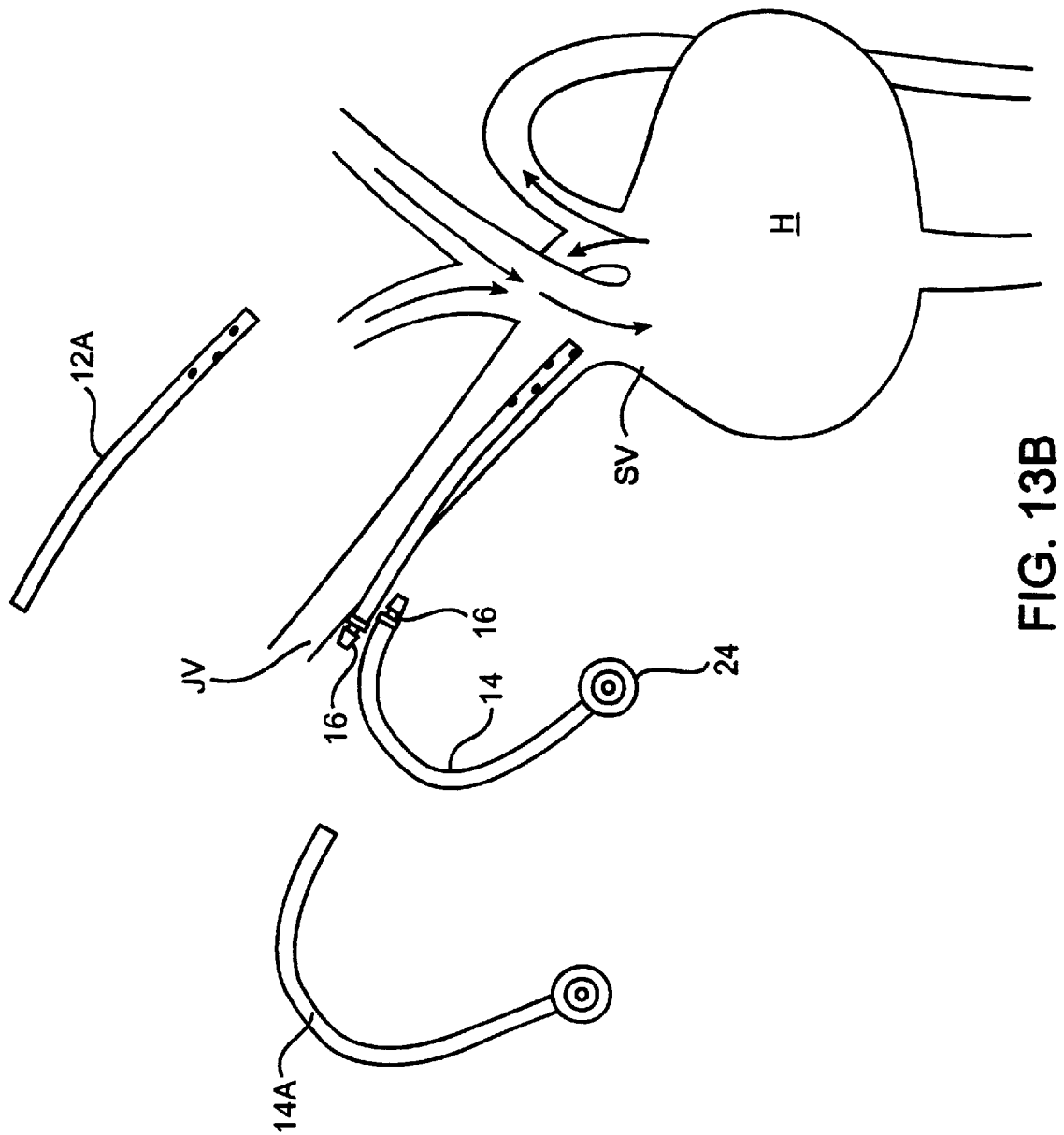
Figure 13C:
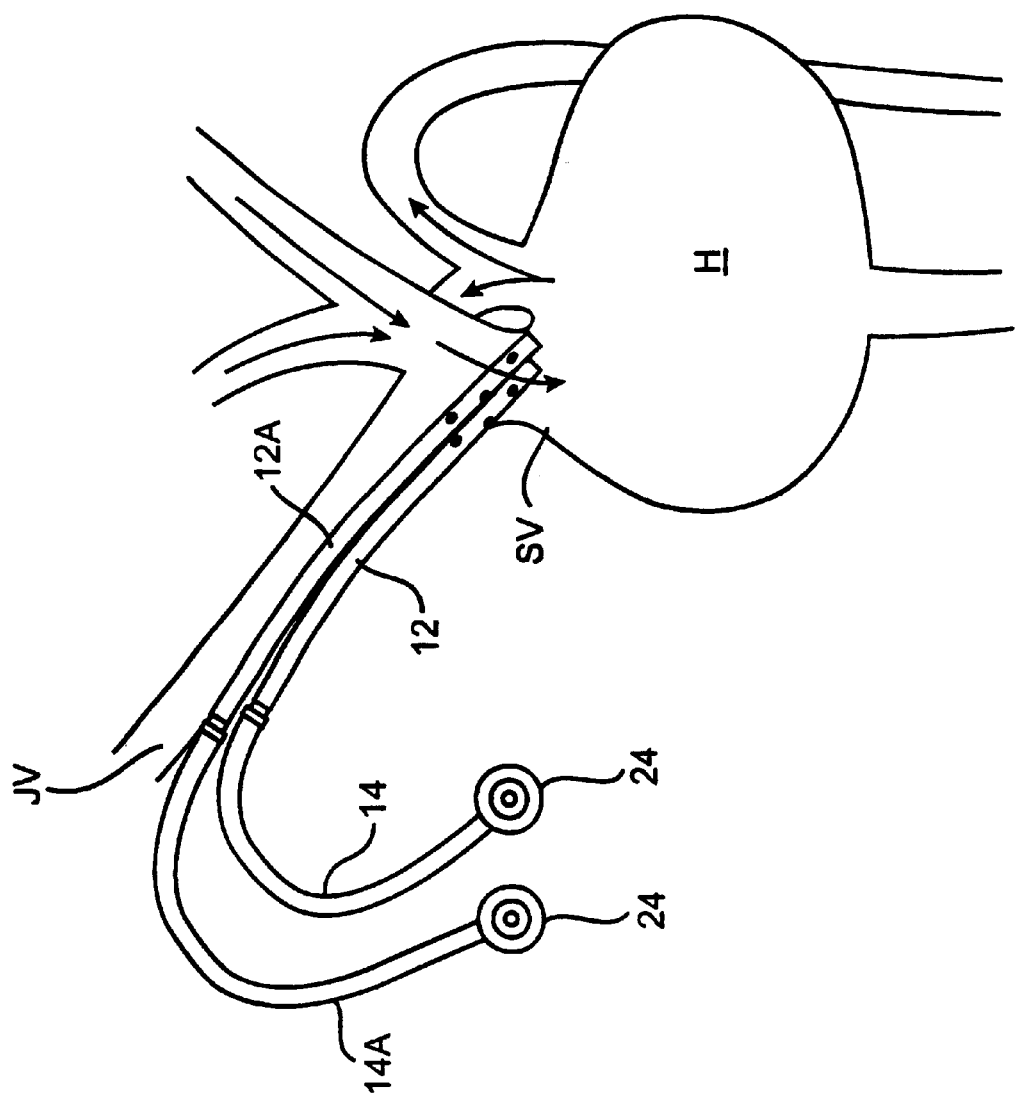

Referring now to FIGS. 13A–13C, replacement of a proximal portion 14 and a distal end 12 of an implanted cannula of the type illustrated in FIG. 1 will be described. A pair of cannulas 10 as shown in FIG. 1 are shown as implanted into the subclavian vein SV. Two pieces of each cannula are joined by a connector 16. After surgically exposing at least a proximal portion of one of the cannulas and a distal end of the other of the cannulas, the proximal portion and distal end may be removed, as shown in FIG. 13B. Replacement sections 14A and 12A may then be reconnected to the previously implanted connectors 16, as shown in FIG. 13C.

Referring now to FIG. 14, a kit 300 comprising at least one cannula component according to the present invention, such as a distal end 12, a proximal portion 14 (optionally with port 24), and/or a connector 16 will be provided together with instructions for use according to any of the replacement protocols described above. Typically, one or more of the kit components will be packaged within a conventional package, such as a pouch P, together with the instructions for use IFU. Preferably, the packaged components will be maintained sterilely. It will be appreciated that the particular cannula component which is selected will depend on the nature of the replacement procedure. Before procedure is begun, the physician will determine what component needs to be replaced and how the attachment is to be made. For example, if only a distal section of a two-piece implanted cannula needs to be replaced, the kit will then include only the replacement distal section together with the instructions for use. If a connector is necessary, the physician may use a kit which contains the connector and a portion of the cannula.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An improved method for replacing an implanted cannula having a distal end attached to a body lumen and a proximal portion disposed remotely from the distal end, wherein the improvement comprises:

surgically exposing a portion of the cannula while leaving at least one of the distal end and the proximal portion unexposed;

disconnecting the cannula within the exposed portion to separate the distal end from the proximal portion;

replacing one of the distal end and the proximal portion with a replacement while leaving the other in place; and reconnecting the cannula by attaching the replacement to the other of the distal end and the proximal portion which had been left in place.

2. An improved method as in claim 1, wherein the surgically exposing step comprises exposing the entire distal end of the cannula, wherein the distal end is replaced.

3. An improved method as in claim 1, wherein the surgically exposing step comprises exposing the entire proximal portion of the cannula, wherein the proximal portion is replaced.

4. An improved method as in claim 3, wherein the surgically exposing step comprises exposing an access port at a proximal portion, wherein the proximal portion and the access port are replaced.

5. An improved method as in claim 1, wherein the distal end and the proximal portion of the implanted cannula are joined by a connector, wherein the surgically exposing step comprises exposing the connector, the disconnecting step comprises removing at least one of the distal end and the proximal portion from the connector, and the reconnecting step comprises attaching at least one of a replacement distal end and a replacement proximal portion to the connector.

6. An improved method as in claim 5, further comprising:

providing a new connector;

replacing the previously implanted connector with the new connector.

7. An improved method as in claim 5, wherein the connector is not replaced and the replacement distal end or replacement proximal portion is attached to the original connector.

8. An improved method as in claim 1, wherein the distal end and the proximal portion of the implanted cannula are formed as a continuous tube and wherein the disconnecting step comprises severing the continuous tube to produce a free implanted end.

9. An improved method as in claim 8, wherein the reconnecting step comprises attaching a connector to the free implanted end of the continuous tube and attaching a tubular replacement section to the connector.

10. A kit comprising:

at least one cannula component selected from the group consisting of a proximal cannula portion, a distal cannula end, and a connector adapted to connect a proximal cannula portion to a distal cannula end; and instructions for use according to any of claims 1 to 9.

* * * * *